United States Patent [19]

Sutcliffe

[11] Patent Number: 5,382,225

[45] Date of Patent: Jan. 17, 1995

[54] UNIVERSAL NIGHT SPLINT

[76] Inventor: Brian L. Sutcliffe, c/o P.O. Box 33, Ephraim, Utah 84627

[21] Appl. No.: 913,294

[22] Filed: Jul. 14, 1992

[51] Int. Cl.⁶ ............................................. A61F 3/00
[52] U.S. Cl. ....................... 602/24; 403/345; 411/162
[58] Field of Search .................. 602/24, 29, 8, 23, 28; 128/60 A, 67 R; 403/410, 282, 345; 192/67 R; 623/44; 482/8; 33/559, 561; 464/160; 74/531; 411/185, 186, 187, 188, 189, 160, 161, 162, 957, 958, 959, 537

[56] References Cited

U.S. PATENT DOCUMENTS 2,525,237 10/1950 Park .................................. 602/28
4,088,129 5/1978 DiGiulio ............................ 602/23

*Primary Examiner*—Richard J. Apley
*Assistant Examiner*—Beverly A. Meindl

[57] ABSTRACT

A plurality of night splints for treatment of different infant foot deformities. The splints comprise a pair of top plates (36a and 37a) with base plates 32 or 33, or foot plates (30 or 30a) having an articulated clutch (67) and clutch socket (68), with a dynamic dorsiflexory splint which is able to correct in multiple planes of adjustment simultaneously. In compound deformity problems the universal night splint allows the following simultaneous functions:

1. abduction/adduction of the foot to the leg,
2. abduction/adduction of the forefoot to the rearfoot,
3. varus/valgus relationship of the rearfoot to the leg,
4. varus/valgus relationship of the forefoot to the rearfoot,
5. dorsiflexion/plantarflexion of the foot and leg, and
6. abduction/adduction of foot and leg to cardinal sagittal plane. The multiple correction capabilities of the splint are made possible by mounting adjustable top plates (36a and 37a) onto adjustable base plates (32), which are in turn mounted either to a spreader bar (23a), or to a back leg assembly (44a), or to both. This physical configuration makes it possible to articulate the feet in multiple planes with a very simple, easy-to-use and adjust splint.

6 Claims, 4 Drawing Sheets

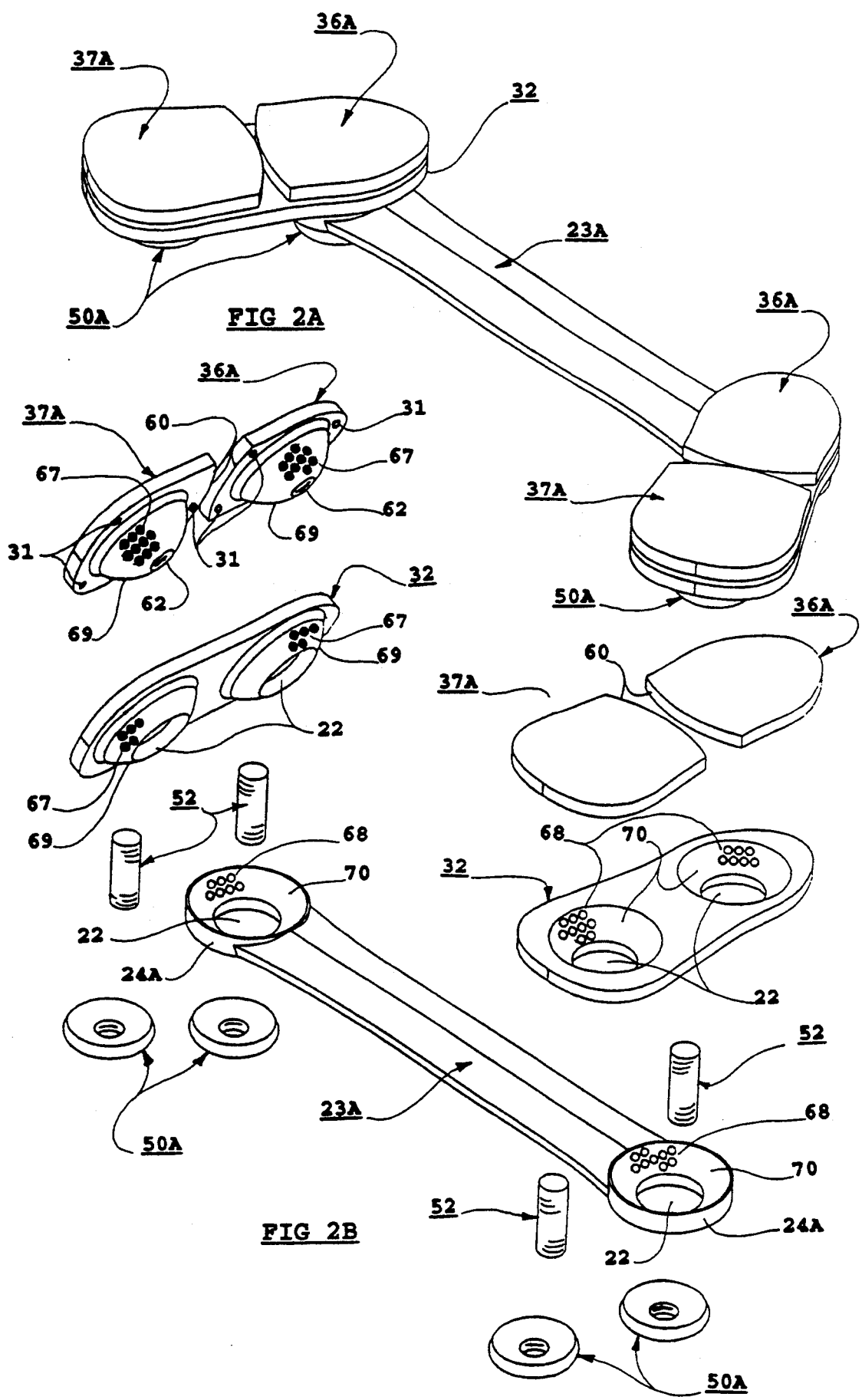

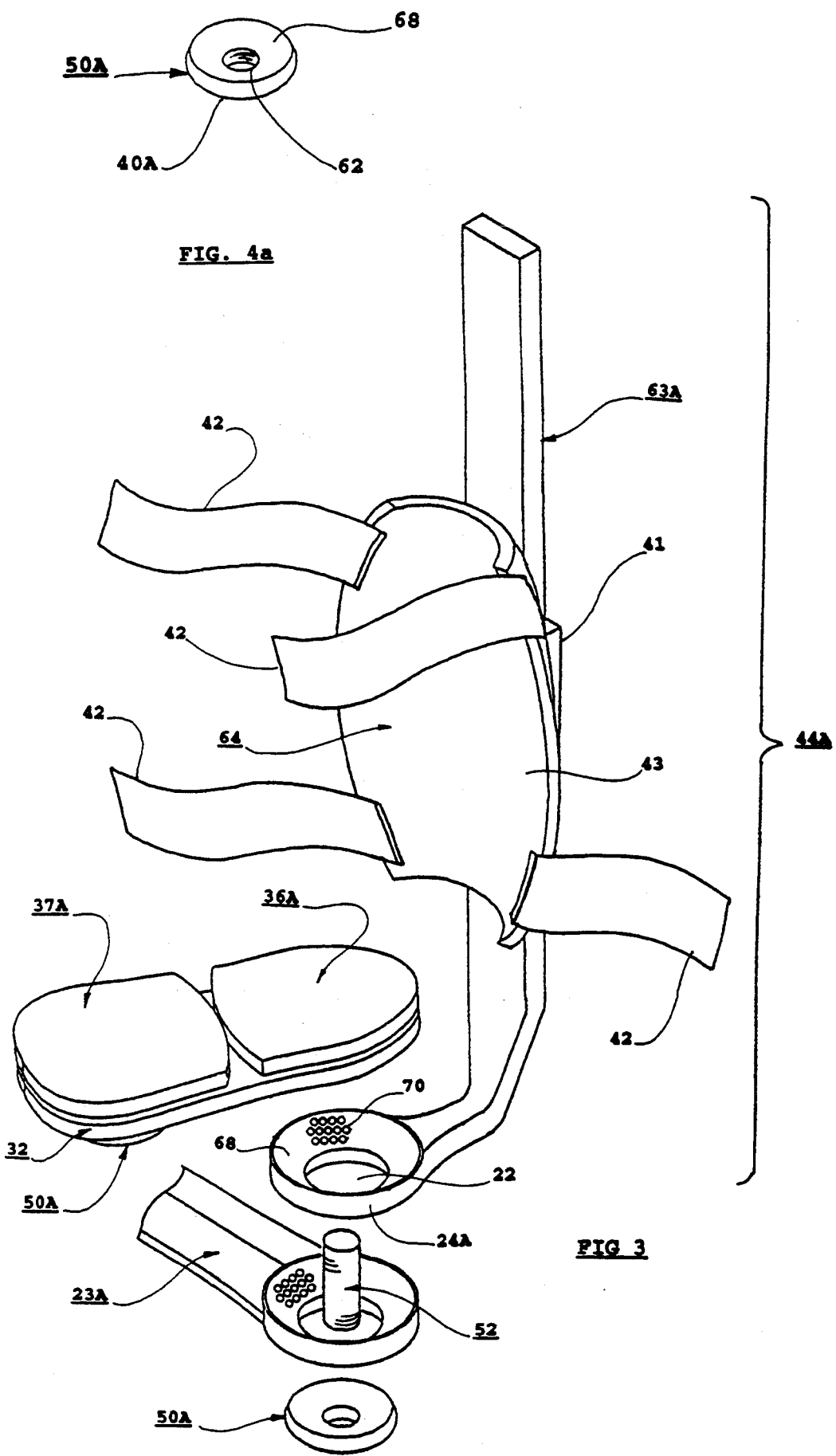

UNIVERSAL NIGHT SPLINT

BACKGROUND—FIELD OF THE INVENTION

This invention relates to an orthopedic foot splint, particularly to one which is useful in correcting bone and positional deformities by holding a patient's feet, and/or legs, in appropriate corrective positions.

BACKGROUND-DISCUSSION OF PRIOR ART

Some children are born with genetic deformities to their feet and many are born with iatrogenic (caused by an outside influence) deformities which are usually caused by growing in an improper position in the womb.

The medical profession treats these deformities with various means which move the bones of the foot into their correct positions. Some physicians choose to withhold treatment, because in a certain percentage of cases the patient will grow out of the problem.

For those physicians who choose to treat the problem, the following methods of treatment are available:
1. casting,
2. surgery, usually followed by casting or splints,
3. orthotic devices or inserts for shoes,
4. orthotic shoes, and
5. braces or splints.

Braces or splints can be used because the bones of the lower extremities in infants and young children are not fully formed and are malleable to a certain extent. Therefore, by encouraging a malformed foot into a new and correct position and holding it there until the foot has adapted to the new and correct position, the malformation of the foot can usually be ameliorated. Splints are in common use to perform this corrective function.

However, currently available splints have been limited in their ability to address the correction of multiple-deformity problems. Therefore, although most splints can be used to treat one deformity, they will not treat any other deformities at the same time. Thus, the other deformities may become fixed and untreatable with splints and require a more invasive and costly treatment, such as surgery.

Although a few prior-art devices have been conceived that could address the problem of multiple deformities, they have not been accepted in the marketplace for various reasons:
1. they are awkward to use,
2. the design is impractical for the use intended,
3. they are difficult to adjust or keep in adjustment,
4. the expense of manufacture is too great, or
5. for reasons of appearance, cost to the patient, or difficulty in application.

This gave rise to the need for a device that could adjust or correct in several planes of adjustment simultaneously that was simple, attractive, cost efficient, easy to install, use, and adjust, etc.

Thus, splints with a rotating wedge and splints with an articulated clutch were conceived to resolve these problems.

One common type of prior-art splint of this type is disclosed U.S. Pat. Nos. 3,910,267, 1974, and 3,973,559, 1975, to Reiman. However, this splint merely hold a patient's feet in a fixed position and has no adjustment capability.

Another splint of this type is shown in U.S. Pat. No. 4,040,416, 1977, to Zentman. Zentman's splint, however, corrects abduction/adduction (toe in/toe out) of the foot to the leg only. Abduction/adduction is the motion occurring on the transverse plane during which the distal aspect of the foot moves away from (abduction), or towards (adduction) the midline of the body about a vertical axis of rotation located at the proximal aspect of the foot.)

U.S. Pat. No. 3,892,231, 1975, to Tummillo does allow for a limited amount of abduction/adduction adjustment between the forefoot and rearfoot ("C" shaped foot or severe flat foot) as well as abduction/adduction of the foot to the leg. The patient's subtalar joint must first be stabilized before the foot is rotated in order to prevent the possibility of causing flat feet. However, this splint does not perform this function. (The subtalar joint is formed by the appositional articular surfaces of the talus and calcaneous.)

Although there are splints, of the type disclosed in U.S. Pat. No. 4,263,901, 1981, to Nichols, that do tilt to stabilize the subtalar joint. These splints tilt and rotate only and are not capable of any other corrective adjustment.

Other common types of prior-art splints, are disclosed in U.S. Pat. Nos. 4,249,523, 1981, to Bidwell, and 4,413,536, 1983, 4,481,940, 1984, and 4,495,943, 1985, to Kurtz. While allowing more mobility to the patient, thereby effectively alleviating the subtalar joint problem, these still correct only abduction/adduction of the foot to the leg. When the patient places one foot close to the other, or crosses the feet even slightly while attempting to walk, parallelogram components in the splint interfere with each other, presenting a trip hazard.

U.S. Pat. No. 3,777,747, 1973, to Friedman shows a splint which requires a specially made shoe to effectively mount to the splint and does not address abduction/adduction of the forefoot to the rearfoot. Friedman's splint is complex and difficult to adjust, especially as a change in one adjustment may require a compensating change to other adjustments.

U.S. Pat. No. 4,570,620, 1986, to Kurtz merely shows a baseplate for a shoe, which is designed for use in conjunction with a splint. By itself this device is capable of torsional adjustment in an oblique plane only and nothing else.

None of the beforementioned splints correct dorsiflexion/plantarflexion problems or are capable of simultaneous correction in all splint correctable planes. (Dorsiflexion/plantarflexion is the motion occurring on the cardinal sagittal plane during which the distal aspect of the foot moves toward (dorsiflexion), or away from (plantarflexion) the tibia about an axis of rotation located at the proximal aspect of the foot. The cardinal sagittal plane is a flat imaginary vertical plane passing through the body from front to back, dividing it into a right half and a left half. Varus/valgus is a fixed structural position which the foot would assume if it were inverted (varus) or everted (valgus)).

OBJECTS AND ADVANTAGES

Accordingly, several objects and advantages of the present invention are to provide an adjustable splint which is capable of tilting the foot to stabilize the subtalar joint, and which allows the patient to be ambulatory.

Other objects and advantages are to provide a splint with additional simultaneous functions, including abduction/adduction of the forefoot to the rearfoot, varus/valgus relationship of the rearfoot to the leg (heel tilting in/out), varus/valgus relationship of the forefoot to the rearfoot (forefoot tilting in/out, heel tilting in/out), dorsiflexion/plantarflexion of the foot and leg, and abduction/adduction of foot and leg to the cardinal sagittal plane.

Simultaneous adjustment of common splint-treatable infant foot deformities may reduce the treatment time required, thereby reducing or even eliminating the need for future surgery.

Another object is to provide a universal splint for use at night. A universal night splint may be easily adjusted to accommodate each patient's required positional correction parameters without disassembly. The universal night splint may be adjusted, either on or off the patient, with precise and prescribable settings.

The universal night splint has the ability to restore the correct position of, and support the arch of the foot. When the foot is operated on to alter its structure, the universal night splint may be utilized to hold or position the foot for x-ray position verification prior to placing a cast on the foot and leg. Casting may be used in conjunction with the universal night splint.

Further features, objects and advantages of the present invention are stated in or will be apparent from the detailed description and drawings of the presently preferred embodiments of the invention.

BRIEF DESCRIPTION OF DRAWING FIGURES

FIG. 1b is an exploded view of the splint of FIG. 1a.

FIG. 2a is a perspective view of an articulated clutch operated quadra-plane embodiment of an assembled universal night splint in accordance with the invention.

FIG. 2b is an exploded view of the splint of FIG. 2a.

FIG. 3 is a perspective view of an articulated clutch operated hexa-plane embodiment of an universal night splint in accordance with the invention.

FIG. 4a is a perspective view of a nut used for articulated clutch operated splints as shown in FIGS. 1a through 3.

LIST OF REFERENCE NUMERALS

| | |
|---|---|
| 22 large hole | 37a top plate, toe portion with articulated clutch |
| 23a bar with chevron cross section and cupped ends | 40a nut body with articulated clutch socket |
| 24a cupped ends | |
| 30a foot plate with articulated clutch | 41 slide guide |
| 31 depressions | 42 retaining strap |
| 32 base plate with articulated clutch elements | 43 calf body |
| | 44a back leg assembly with articulated clutch |
| 36a top plate, heel portion with articulated clutch | 50a nut for articulated clutch |
| 60 arc | 52 rigid bolt |
| 62 threaded hole | 63a vertical adaptor with articulated clutch |
| | 64 calf cup |
| | 67 male articulated clutch |
| | 68 articulated clutch socket |
| | 69 slightly protruding knobs |
| | 70 shallow detents |

DESCRIPTION OF UNIVERSAL NIGHT SPLINT

The presently preferred embodiments of the universal night splint are depicted in FIGS. 1a through 4b, and include shoes (not shown) which the patient wears when using the splint.

The splint has right and left hand sides which are both assembled in like manner, therefore assembly of only one side is described. The patient's shoe (not shown) may be affixed to the splint by screws, rivets, glue, or any other appropriate means, well-known in the art.

The names of the various embodiments of the universal night splint refer to the operant mechanism, and the number of planes or types of adjustment which that particular embodiment is capable of, or commonly used for, correcting.

Splints of this type are usually worn at night when the patient is sleeping because of restriction to the patient's mobility (hence the term "night splint").

Structure-Articulated Clutch Bi-Plane Embodiment

Figure 1A:
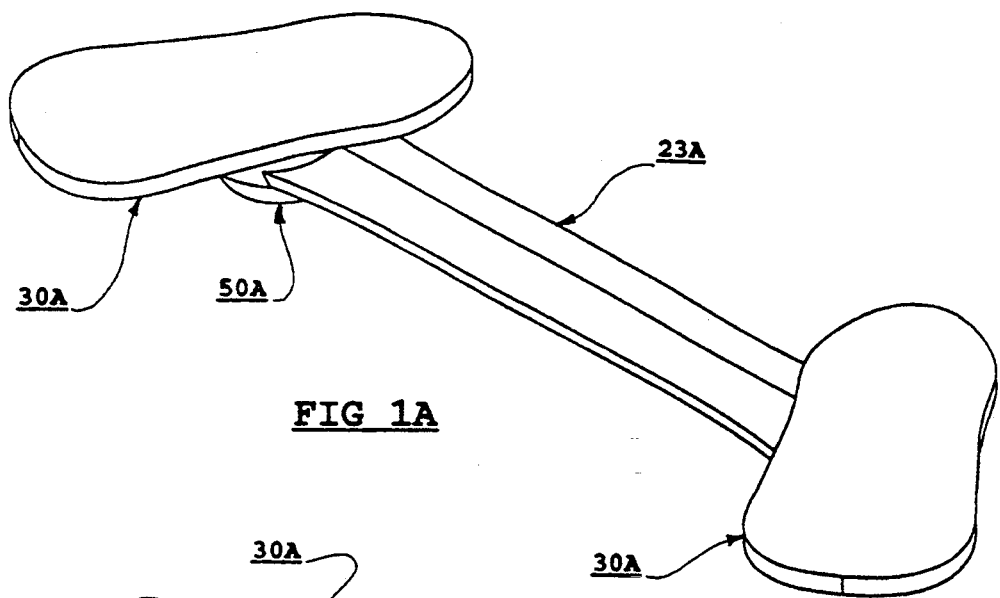
FIG. 1a is a perspective view of an articulated clutch operated bi-plane embodiment of an assembled universal night splint in accordance with the invention.
Figure 1B:
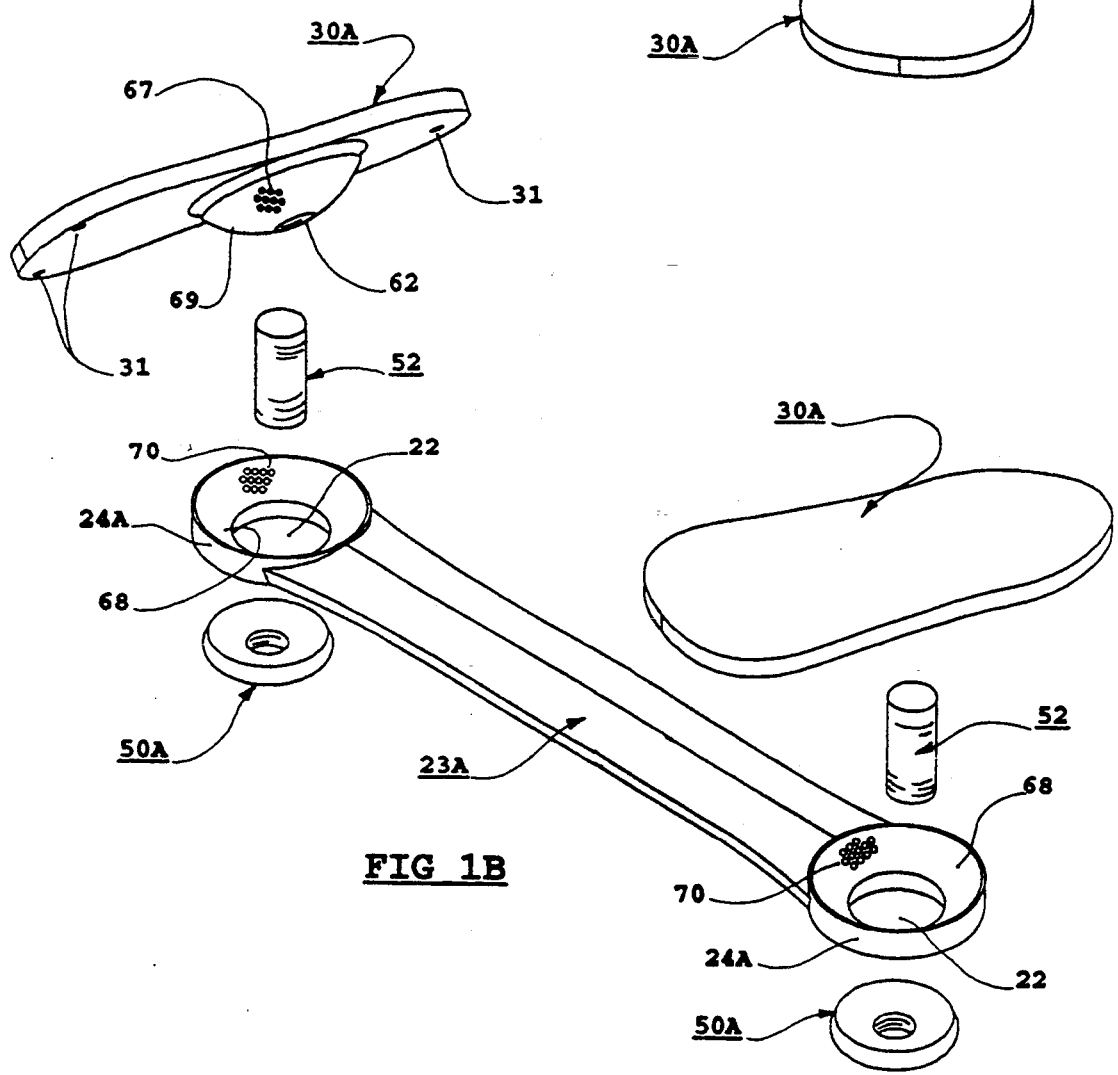
Figure 4B:
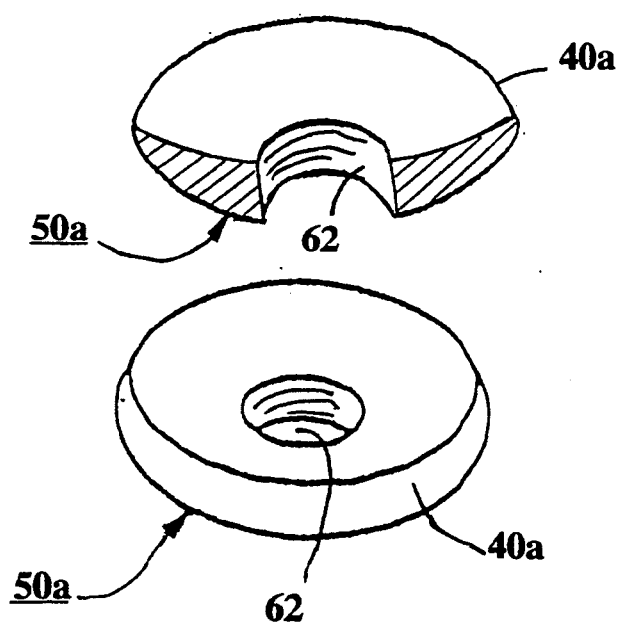
FIG. 4b is a sectional view of a nut used for articulated clutch operated splints as shown in FIGS. 1a through 6.

FIGS. 1a and 1b show a splint for treatment of abduction/adduction of the foot to the leg. This splint comprises foot plates 30a, bolts 52, a spreader bar 23a, and nuts 50a.

Detail-Articulated Clutch Bi-Plane Embodiment

The top view of plate 30a, as shown in FIGS. 1a and 1b, is an approximation of the outline of a shoe. The plate 30a is comprised of a planar upper-surface for receiving the shoe (not shown) of the patient. The under-surface of plate 30a has depressions 31 for locating the fasteners (not shown) used to affix the shoe of the patient, and has a male articulated clutch 67 with slightly protruding knobs 69 and a hole 62 extending through its center.

The bar 23a as shown in FIGS. 1a through 4b comprises cupped ends 24a on each end of a chevron cross-sectioned middle portion. The cupped ends 24a each have articulated clutch sockets 68 in the upper-surface and holes 22 extending through their centers. The sockets 68 have shallow detects 70 in a regular array on thier surfaces. The under-surfaces of cupped ends 24a each have clutch 67.

The nut 50a comprises a nut body 40a, with a socket 68 and a blind hole 62 in its upper-surface. Alternatively, the body 40a of the nut 50a can also be made from a rubber or plastic material in a size approximately the width of the patient's foot, and in a configuration suitable for walking on (not shown).

Assembly-Articulated Clutch Bi-Plane Embodiment

To assemble the splint, the patient's shoe is affixed to the plate 30a, which is in turn inserted into the bar 23a. The assembly is held in place and secured by a nut 50a and bolt 52.

Operation-Articulated Clutch Bi-Plane Embodiment

For treatment of abduction/adduction of the foot to the leg, the nut 50a is loosened, then the shoe and plate 30a are tilted to the angle necessary to stabilize the subtalar joint and rotated to the desired toe-in/toe-out position. Then the assembly is fixed in position by re-tightening the nut 50a. Tightening the nut 50a applies tension between the plate 30a and nut 50a by means of a bolt 52, thereby positively engaging the clutch 67 knobs 69 and socket 68 detents 70.

Structure-Articulated Clutch Quadra-Plane Embodiment

FIGS. 5a and 5b show a splint for treatment of abduction/adduction of the foot to the leg, abduction/adduction of the forefoot to the rearfoot, varus/valgus relationship of the rearfoot to the leg, and varus/valgus relationship of the forefoot to the rearfoot. The splint comprises top plates 36a and 37a, base plates 32, bolts 52, a bar 23a, and nuts 50a.

Detail-Articulated Clutch Quadra-Plane Embodiment

The top view of plates 36a and 37a is similar to plate 30. However, plates 36a and 37a are divided into two portions by the arcs 60. Plates 36a and 37a, as shown in FIG. 2a through 6, comprises a planar upper-surface for recieving the shoe of the patient. The under-surface of each has depressions 31 for locating the fasteners (not shown) used to affix the splint to the shoe of the patient, and has a clutch 67 with knobs 69 with a hole 62 extending through its center.

The plate 32, as shown in FIG. 2a through 3 comprises a planar upper-surface, with sockets 68 in the toe and heel portions. A clutch 67 protrudes from the under-surface opposite each socket 68. The sockets 68 have detents 70, clutches 67 have knobs 69 with a hole extending through the center of each clutch 67.

Assembly-Articulated Clutch Quadra-Plane Embodiment

The sole of the patient's shoe is split into a heel and toe portion and then affixed to plates 36a and 37a, which are in turn inserted into the plate 32. The assembly is then inserted into the bar 23a and held in place and secured by nuts 50a and bolts 52.

Operation-Articulated Clutch Quadra-Plane Embodiment

Treatment of abduction/adduction of the foot to the leg and varus/valgus relationship of the rearfoot to the leg is accomplished in a similar manner as with the articulated clutch biplane splint embodiment. For treatment of abduction/adduction of the forefoot to the rearfoot, and varus/valgus relationship of the forefoot to the rearfoot, nuts 50a are loosened and plates 36a and 37a are rotated and tilted about their vertical axes to a corrective position. Tightening nuts 50a applies tension between plates 36a and 37a and nuts 50a by means of bolts 52, thereby positively engaging the clutch 67 knobs 69 and socket 68 detents 70.

Structure-Articulated Clutch Hexa-Plane Embodiment

FIG. 3 shows a splint for treatment of abduction/adduction of the foot to the leg, abduction/adduction of the forefoot to the rearfoot, varus/valgus relationship of the rearfoot to the leg, varus/valgus relationship of the forefoot to the rearfoot, and for dorsiflexion/plantarflexion and equinus/equino problems. The splint is an articulated clutch quadra-plane embodiment with the addition of back leg assemblies 44a. One back leg assembly 44a comprises a cup 64, and a vertical adaptor 63a.

Detail-Articulated Clutch Hexa-Plane Embodiment

The adaptor 63a comprises a bar 71 which is bent on one end with a cupped end 24a on the bent end. The cupped end 24a has a clutch 67 on its under-surface, a socket 68 with detents 70 on its upper-surface and a hole 22 extending through its center.

Assembly-Articulated Clutch Hexa-Plane Embodiment

The adaptor 63a is inserted into the guide 41 of cup 64. Then this assembly is inserted between the bar 23a and nut 50a of the articulated clutch quadra-plane splint embodiment.

Operation-Articulated Clutch Hexa-Plane Embodiment

Abduction/adduction, and/or varus/valgus problems are corrected as with the articulated clutch quadra-plane splint embodiment described previously. For dorsiflexion/plantarflexion and equinus/equino problems, the angular relationship between the adaptor 63a and spreader bar 23a is adjusted by loosening the nut 50a, repositioning the angle of the adaptor 63a to the prescribed adjustment angle and then re-tightening nuts 50a. By removing the bar 23a and using the walking nut described previously, the patient may be ambulatory. Varus/valgus problems without the bar 23 are corrected in a like manner as above.

SUMMARY, RAMIFICATIONS AND SCOPE

The reader will see that I have described an orthopedic foot splint with the capability of multiple simultaneous corrections. The facility of multiple simultaneous correction is made possible, in part, by placing top plates (36a and 37a) on moveable base plates 32 or 33. The ease of multiple simultaneous correction is made possible, in part, by the articulated clutch 67 and socket 68. The articulated clutch 67 and socket 68 allow a relatively simple device to achieve a very broad range of adjustments without complicated setup or complex instructions.

Rotation correction alone stresses the patient's subtalar joint, thereby possibly causing flat feet. The simplest embodiment of this splint will rotate and tilt in any direction approximately normal to the axis of rotation. Tilting stabilizes the patient's subtalar joint thus preserving the arch of the foot and preventing a possible causative deformity. The other embodiments will simultaneously treat increasingly complex and difficult deformities, thus effectively reducing the necessity of sequential treatment in many cases and the problems associated with the delays.

The universal night splint is a small, lightweight, easily installed and adjusted, attractively designed medical device that will perform multiple simultaneous correction of, and adjustment to, infant or child foot deformities.

The universal night splint is applied to foot deformities, such as calcaneal varus, calcaneal valgus, vertical talus, metatarsus adductus, metatarsus adductal varus, metatarsus adductal valgus, talipes equinas, talipes equino valgus, talipes equino varus, and talipes equino adducto varus.

The universal night splint has the capability of making each foot and leg completely independent of the other for walking purposes.

Although the description above contains many specificities with respect to exemplary embodiments thereof, these should not be construed as limiting the scope of the invention but as merely providing illustrations of the presently preferred embodiments. It will be understood by those of ordinary skill in the art that variations and modifications may be affected within the scope and spirit of the invention. For example, bar 23 can have other cross-sectional shapes, etc. The specific materials and dimensions indicated can be changed to other suitable materials and dimensions. Thus the scope of the invention should be determined by the appended claims and their legal equivalents, rather than by the examples given.

What is claimed is:

1. An orthopedic foot splint adapted to be attached to the shoes or feet of a patient comprising:
   a. a pair of foot plates adapted to be affixed to the shoes or feet of a patient, and
   b. an elongated bar interconnecting said foot plates,
   c. means for enabling said foot plates to rotate and tile with respect to said bar further comprising:
      a male cupped articulated clutch mounted to the underside of each of said plates having slightly protruding knobs arranged in a regular array on the interfacing surface and cupped articulated clutch sockets positioned on the ends of said bar having shallow detents arranged in a regular array on the interfacing surface,
   whereby tilting and rotating can be accomplished with said cupped clutch components, so that the patient's feet can be tilted to protect subtalar joint.

2. An orthopedic foot splint as in claim 1 further comprising a pair of bolts and a corresponding pair of nuts for fixing said male cupped articulated clutches in alignment with said cupped articulated clutch sockets whereby said knobs of said male cupped articulated clutches engages said detents said cupped male cupped articulated clutches engage said detents of said cupped articulated clutch sockets to form positive, prescribable adjustments of said splint for the purpose of correcting positional deformities.

3. An orthopedic foot splint adapted to be attached to the shoes or feet of a patient comprising:
   a. a pair of two-piece top plates adapted to be affixed to the shoes of feet of a patient,
   b. a pair of two-piece base plates situated below said top plates,
   c. means for enabling said top plates to rotate or tile with respect to said base plates further comprising:
      a pair of male cupped articulated clutches mounted to the underside of each of said top plates having slightly protruding knobs arranged in a regular array on the interfacing surface and a pair of cupped articulated clutch sockets positioned on the top side of said base plates having shallow detents arranged in a regular array on the interfacing surface,
   d. an elongated bar interconnecting said base plates,
   e. means for enabling said base plates to rotate and tilt with respect to said bar further comprising:
      a pair of male cupped articulated clutches mounted to the underside of each of said base plates having slightly protruding knobs arranged in a regular array on the interfacing surface and cupped articulated clutch sockets positioned on the ends of said bar having shallow detents arranged in a regular array on the interfacing surface,
   whereby tilting and rotating can be accomplished with said cupped articulated clutch components, so that the patient's feet can be tilted to protect the subtalar joint.

4. An orthopedic foot splint as in claim 3 further comprising a pair of bolts and a corresponding pair of nuts for fixing said male cupped articulated clutches in alignment with said cupped articulated clutch sockets whereby said knobs of said male cupped articulated clutches engage said detents of said cupped articulated clutch sockets to form positive, prescribable adjustments of said splint for the purpose of correcting positional deformities.

5. An orthopedic foot splint as in claim 3, wherein the proximate edges of said top plates are cupped so as to preclude the presentation of sharp edges to the feet of the patient during use on the splint.

6. An orthopedic foot splint as in claim 3, further comprising:
   a. a pair of calf cups for affixing said splint to the patient's legs,
   b. means for enabling said calf cups to rotate and tile with respect to said elongated bar, and
   c. a pair of vertical adaptors for rotating and tilting said calf cups, and said vertical bars with respect to said elongated bar,
whereby dorsiflexion/plantarflexion and equinus-/equino problems can be corrected.

* * * * *